United States Patent [19]

Imai et al.

[11] Patent Number: 5,083,283

[45] Date of Patent: Jan. 21, 1992

[54] METHOD OF DETERMINING CALIBRATION CURVE AND APPARATUS USING CALIBARATION CURVE

[75] Inventors: Kyoko Imai, Katsuta; Yasushi Nomura, Mito; Hiroshi Umetsu, Katsuta, all of Japan

[73] Assignee: Hitachi, Ltd., Toyko, Japan

[21] Appl. No.: 323,490

[22] Filed: Mar. 14, 1989

[30] Foreign Application Priority Data

Mar. 18, 1988 [JP] Japan .................. 63-63192

[51] Int. Cl.$^5$ ........................... G01N 31/00
[52] U.S. Cl. .................. 364/497; 364/481; 364/571.02; 426/8; 426/34
[58] Field of Search .............. 364/581, 577, 571.01, 364/571.02, 497, 498, 572, 554; 73/863, 864, 1 R; 436/8, 34, 43, 164; 250/564, 565

[56] References Cited

U.S. PATENT DOCUMENTS

| | | | |
|---|---|---|---|
| 3,960,497 | 6/1976 | Acord | 364/497 X |
| 3,998,591 | 10/1976 | Killer | 250/565 |
| 4,043,756 | 8/1977 | Sommervold | 436/43 |
| 4,128,339 | 12/1978 | Yamazaki et al. | 250/565 |
| 4,169,125 | 9/1979 | Rodriguez et al. | 364/497 X |
| 4,488,812 | 12/1984 | Kraft et al. | 250/564 X |
| 4,539,295 | 9/1985 | Blough, Jr. | 436/164 X |
| 4,636,360 | 1/1987 | Sakurada et al. | 436/164 X |
| 4,642,778 | 2/1987 | Hieftje et al. | 364/497 X |
| 4,658,367 | 4/1987 | Potter | 364/572 X |
| 4,678,755 | 7/1987 | Shinohara et al. | 436/43 |
| 4,867,908 | 9/1989 | Recktenwald et al. | 436/8 X |
| 4,884,213 | 11/1989 | Iwata et al. | 364/498 |
| 4,958,295 | 9/1990 | Davidson et al. | 364/497 |

*Primary Examiner*—Joseph L. Dixon
*Attorney, Agent, or Firm*—Fay, Sharpe, Beall, Fagan, Minnich & McKee

[57] ABSTRACT

A method of determining a calibration curve used in deciding the components of living organism by means of the least-squares method by using a plurality of measured data at different concentrations obtained by measuring reaction solutions of a plurality of standard substances having different concentrations. At least a single set of measured data $Y(i)$ is weighted in a predetermined manner, the measured data $Y(i)$ being obtained from the standard substance reaction solution at a specific concentration $X(i)$ near a limit value used in deciding the living organism components. With the weighting, a calibration curve having a high precision at a portion near the limit value is realized resulting in a correct and highly reliable decision.

4 Claims, 4 Drawing Sheets

DISPLAY SCREEN

AFP (mg/ml)

METHOD OF DETERMINING CALIBRATION CURVE AND APPARATUS USING CALIBARATION CURVE

BACKGROUND OF THE INVENTION

The present invention relates to a method of determining a calibration curve and an automatic analyzer using this calibration curve. More particularly, the invention relates to a method of determining a calibration curve suitable for precisely measuring a limit value (cutoff value) to be used as a decision criterion in analyzing the components of a living organism, and an automatic analyzer using this calibration curve.

A conventional method of determining a calibration curve is known as disclosed in U.S. Pat. No. 3,998,591 and Japanese Patent Laid-open Publication JP-A-60-73436.

Instead of a straight calibration line conventionally used by the enzyme immunoassay (EIA) for chemical inspections at clinics, a calibration curve is generally used in testing immunoreaction through EIA. In addition, the shape of a calibration curve is susceptible to change with the type of measuring systems and reaction conditions. EIA is an assay for micro substance so that it is often performed near a limit value of detection, thus posing a problem of a relatively large variation of measured data of standard substances for respective concentrations. The theoretical formula of a calibration curve of EIA can be obtained if the antigen-antibody reaction based on which the measurement is carried out can be quantitatively analyzed. The formula is generally a complicated non-linear function which is very difficult to be dealt with statistically so that an empirical formula is often used. In either case, it becomes necessary to prepare a regression model to regress the calibration curve and solve the concentration of an unknown sample substance. As a regression model, there are known logistic curves, For instance, the following model is known:

$$Y(i) = R_o + \frac{K}{1 \times \exp\{-a+b\ln X(i)\}} \quad (1)$$

where $K = R_\infty - R_o$, $R_0$: a response for a standard substance (sample) with 0 (zero) concentration $R_\infty$: a response for a standard substance (sample) with infinite concentration a, b: parameter $X(i)$: standard substance (sample)

$Y(i)$: measured data (e.g., absorptivity data)

A conventional method of determining a calibration curve uses measured data per se of standard substances (samples). In other words, the conventional method determines a calibration curve without paying particular attention to the measured data near the cutoff value to be used in analyzing the components of living organism, in spite of the fact that the cutoff value plays an important role in diagnosing disease or pathology. Generally the average values of measured data of standard substances for respective concentrations are processed (through least-squares approach) to obtain the calibration curve.

Recently, high sensitivity immunoassays have been developed and the operation of measuring data is highly automated. For instance, substances associated with infectious disease can now be automatically measured contrary to the conventional manual operation. Different from an ordinary quantitative measurement, immunoassays aim at a qualitative measurement through which it is decided if an object substance is present in a specimen. For instance, it is checked if there is an antibody of HIV (i.e., AIDS) to decide whether or not the patient is infected with AIDS. Taking as an example a cancer marker AFP (α-fetoprotein) commonly undergoing a quantitative measurement, for a screening test, to check the measured AFP value itself is not as important as to check if the measured AFP value falls within the range of values for a normal person or for a cancer patient. A limit value for such decision criterion is called a cutoff value. In order to reliably decide whether a person is infected with AIDS or cancer if the measured value of a specimen is higher than a cutoff value, and not infected if it is lower than the cutoff value, the data measured near the cutoff value are required to be more precise than the data for other concentrations. It is also necessary to use a calibration curve which well matches the concentrations at the concentration range near the cutoff value than at the other concentration ranges.

The conventional method of determining a calibration curve, however, processes a plurality of measured data of standard substances without weighting the data in a particular concentration range, for example, the data near the cutoff value, to thus make the calibration curve well match measured data. The conventional method takes the necessary measures for reducing the adverse effects of data variation by increasing the number of measurements of a standard substance near the cutoff value and using the average value thereof. However, in determining the calibration curve, the average values of the measured data near the cutoff value are processed in the similar manner as the average values at the other concentrations, without taking into consideration weighting the data near the cutoff value.

SUMMARY OF THE INVENTION

It is therefore a first object of the present invention to provide a method of determining a calibration curve having a high precision at a portion where data within a particular concentration range of a standard substance are used.

It is a second object of the present invention to provide an automatic analyzer having means for partially weighting the data within a particular concentration range.

The first object can be achieved by the method of forming a calibration curve using data of a plurality of reaction solutions having different concentrations of a standard substance, which method determines a calibration curve by processing through partial weighting of data within a particular concentration range. The second object can be achieved by the automatic analyzer having a sample feeding unit for installing a plurality of standard substances having different concentrations and a sampling unit for sampling the standard substances plural times, which automatic analyzer comprises first means for partially weighting the data within a particular concentration range of the data of reaction solutions of the standard substances, second means for processing the data weighted by first means, third means for determining a calibration curve based on the data processed by second means, and fourth means for displaying the determined calibration curve.

Various methods are possible to weight the measured data. According to a first method, the number of data are increased by measuring a standard substance plural times at a specific concentration, and the data are separately and independently processed. Since the number of data at the specific concentration is large as compared with the data at the other concentrations, the specific concentration can be weighted. According to a second method, the number of data of a standard substance at a specific concentration is increased by n multiple by means of data processing to obtain a larger number of data than that at the other concentrations. The data are separately and independently processed to determine a calibration curve. According to a third method combining the first and second methods, the cutoff value used in analyzing the components of living organism can be measured with high precision.

According to the automatic analyzer, the data of reaction solutions of standard substances within a particular concentration region are partially weighted and processed to determine a calibration curve. Therefore, the similar advantageous effects as above can be obtained.

DESCRIPTION OF THE PREFERRED EMBODIMENTS

The invention will be described in detail in connection with the embodiments shown in FIGS. 1 to 5.

Figure 1:
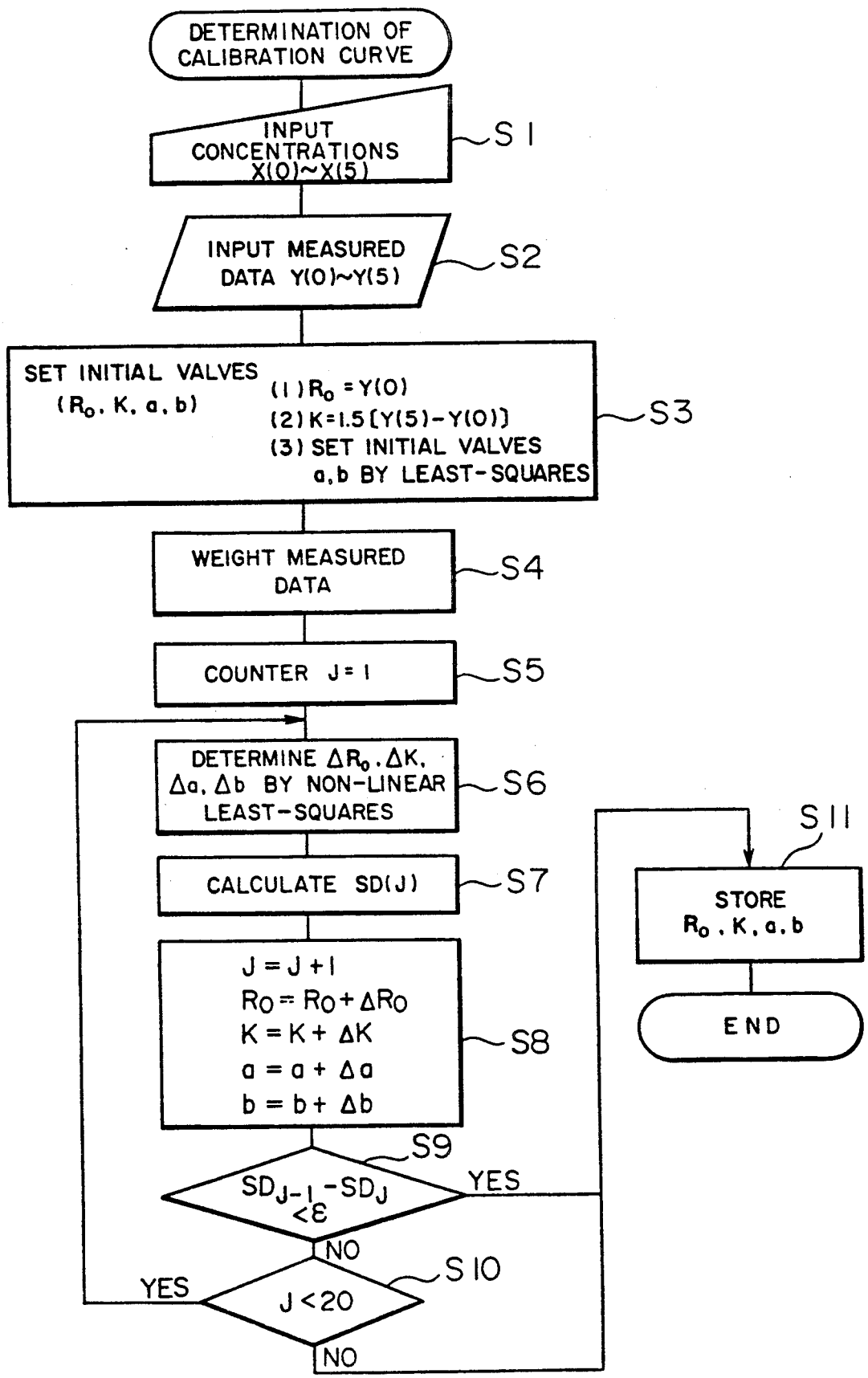
FIG. 1 is a flow chart illustrating the calibration curve determining method according to an embodiment of this invention.

FIG. 1 is a flow chart illustrating multi-regression through the non-linear least-squares approach, the flow chart being used for explaining an embodiment of the calibration curve determining method of this invention. It is assumed that the measured data of a standard substance for a certain test item at concentrations X(0), X(b 1), X(2), X(3), X(4) and X(5) are Y(0), Y(1), Y(2), Y(3), Y(4) and Y(5), respectively. At step S1 shown in FIG. 1, the concentrations X(0) to X(5) for the certain test item are stored in a memory of a central processing unit 51 shown in FIG. 3. At step S2, the measured data Y(0) to Y(5) are stored in a predetermined memory.

Using the stored concentrations and measured data, at step S3, the initial values of four parameters $R_0$, K, a and b shown in the formula (1) are set as indicated by (1) to (3) in the block of step S3.

It is further assumed that the concentration to be weighted is X(1). Then, data Y(1) are increased for use in data processing into Y(11), Y(12), Y(13), Y(14) and Y(15), where Y(11)=Y(12)=Y(13)=Y(14)=Y(15)=Y(1). These values Y(1), Y(11), Y(12), Y(13), Y(14) and Y(15) are independently used and subjected to multi-regression through the non-linear least-squares approach using the Gauss-Newton conversion method, to thereby determine four parameters $\Delta R_0$, $\Delta K$, $\Delta a$ and $\Delta b$ (steps S4 to S6).

The multi-regression method will be detailed. Differences y(ij) between measured data Y(ij) for a certain test item and calculated values F(ij) obtained by substituting the determined parameters into the formula (1) are approximately given by:

$$y(ij) = Y(ij) - F(ij) \simeq \frac{\partial F(ij)}{\partial R_o} \cdot \Delta R_o + \frac{\partial F(ij)}{\partial K_o} \cdot \Delta K_o + \frac{\partial F(ij)}{\partial a} \cdot \Delta a + \frac{\partial F(ij)}{\partial b} \cdot \Delta b$$

Figure 5:
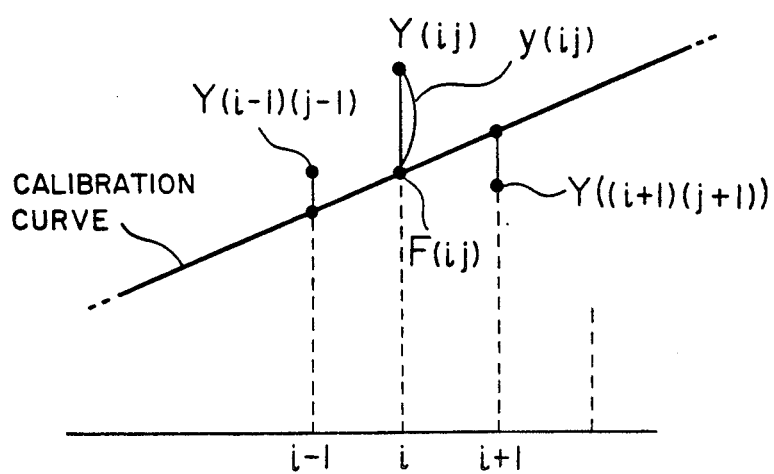
FIG. 5 shows measured values, calculated values and differences therebetween.

The relationship among measured data Y(ij), calculated values F(ij) and differences y(ij) is shown in FIG. 5. The parameters to be obtained take the values when the sum S of squares of the differences become minimum. The sum S is written as:

$$S = \Sigma \{y - y(ij)\}^2 = \Sigma \left\{ y - \left( \frac{\partial F(ij)}{\partial R_o} \cdot \Delta R_o + \frac{\partial F(ij)}{\partial K_o} \cdot \Delta K_o + \frac{\partial F(ij)}{\partial a} \cdot \Delta a + \frac{\partial F(ij)}{\partial b} \cdot \Delta b \right) \right\}^2 \quad (2)$$

Since the following equation stands, $$\frac{\partial S}{\partial a} = \frac{\partial S}{\partial b} = \frac{\partial S}{\partial K_o} = \frac{\partial S}{\partial R_o} = 0$$

let $$\frac{\partial F(ij)}{\partial R_o} = x_1, \quad \frac{\partial F(ij)}{\partial K_o} = x_2,$$

$$\frac{\partial F(ij)}{\partial a} = x_3, \quad \frac{\partial F(ij)}{\partial b} = x_4$$

then the four formulas (3) to (6) are established:

$$\Delta R_0 \Sigma x_1{}^2 + \Delta K_0 \Sigma x_1 x_2 + \Delta a \Sigma x_1 x_3 + \Delta b \Sigma x_1 x_4 = \Sigma x_1 y \quad (3)$$

$$\Delta R_0 \Sigma x_1 x_2 + \Delta K_0 \Sigma x_2{}^2 + \Delta a \Sigma x_2 x_3 + \Delta b \Sigma x_2 x_4 = \Sigma x_2 y \quad (4)$$

$$\Delta R_0 \Sigma x_1 x_3 + \Delta K_0 \Sigma x_2 x_3 + \Delta a \Sigma x_3{}^2 + \Delta b \Sigma x_3 x_4 = \Sigma x_3 y \quad (5)$$

$$\Delta R_0 \Sigma x_1 x_4 + \Delta K_0 \Sigma x_2 x_4 + \Delta a \Sigma x_3 x_4 + \Delta b \Sigma x_4{}^2 = \Sigma x_4 y \quad (6)$$

The increments $\Delta R_0$, $\Delta K_0$, $\Delta a$ and $\Delta b$ of the parameters satisfying the formulas (3) to (6) can be obtained by solving the following matrix equation (7):

$$\begin{bmatrix} \Sigma x_1{}^2 & \Sigma x_1 x_2 & \Sigma x_1 x_3 & \Sigma x_1 x_3 & \Sigma x_1 y \\ \Sigma x_1 x_2 & \Sigma x_2{}^2 & \Sigma x_2 x_3 & \Sigma x_2 x_3 & \Sigma x_2 y \\ \Sigma x_1 x_3 & \Sigma x_3 x_2 & \Sigma x_3{}^2 & \Sigma x_3 x_4 & \Sigma x_3 y \\ \Sigma x_1 x_4 & \Sigma x_4 x_2 & \Sigma x_4 x_3 & \Sigma x_4{}^2 & \Sigma x_4 y \end{bmatrix} \quad (7)$$

Using the obtained $\Delta a$, $\Delta b$, $\Delta K_0$, and $\Delta R_0$, and replacing the parameters with $a = a + \Delta a$, $b = b + \Delta b$, $K_0 = K_0 + \Delta K_0$, and $R_0 = R_0 + \Delta R_0$, the parameters at the minimum sum S of squares are obtained through multi-regression. In the example shown in FIG. 1, the regression is repeated 20 times. The obtained parameters are substituted into the formula (1) to determine a calibration curve having a linear relation to the concentration (steps S7 to S10).

The obtained calibration curve has been weighted for the data at a specific concentration $X(1)$ so that the calibration curve determined with a portion near the specific concentration $X(1)$ well matches the measured data $Y(1)$, to thus allow a high precision of data near the specific concentration $X(1)$.

As appreciated from the foregoing description, in order to process the measured data while weighting the data at a concentration $X(i)$, the number of measured data to be weighted at a concentration $X(i)$ is increased by n multiple prior to the data processing to make the number larger than that at the other concentrations $X(i')$. Namely, the data are transformed into $Y(i1)$, $Y(i2)$, ..., $Y(in)$. The increased number of data as well as the other data are processed not as the averages but as independent data. For this purpose, obtained are the parameters satisfying the condition that the sum of squares of differences between independent data and calculated values $F(ij)$ becomes minimum.

The above-described weighting follows the first method. Specifically, n types of data $Y(i1)$ to $Y(in)$ are actually measured and these data are used in data processing.

In applying the second weighting method, only a single set of data $Y(i)$ are actually measured for weighting the concentration $X(i)$. The data $Y(i)$ are increased by n multiplier through data processing and thereafter, the parameters are calculated which satisfy, as described previously, the condition that the sum of squares of differences between respective data and calculated values $F(ij)$ becomes minimum.

In applying the third weighting method combining the first and second methods, data used for processing in weighting the concentration $X(i)$ are $Y(i) \times n1$, $Y(i+1) \times 1$, $Y(i+2) \times n2$, ..., $Y(i+n) \times n3$, where n1, n2 and n3 are the values of multipliers described above.

Figure 2:
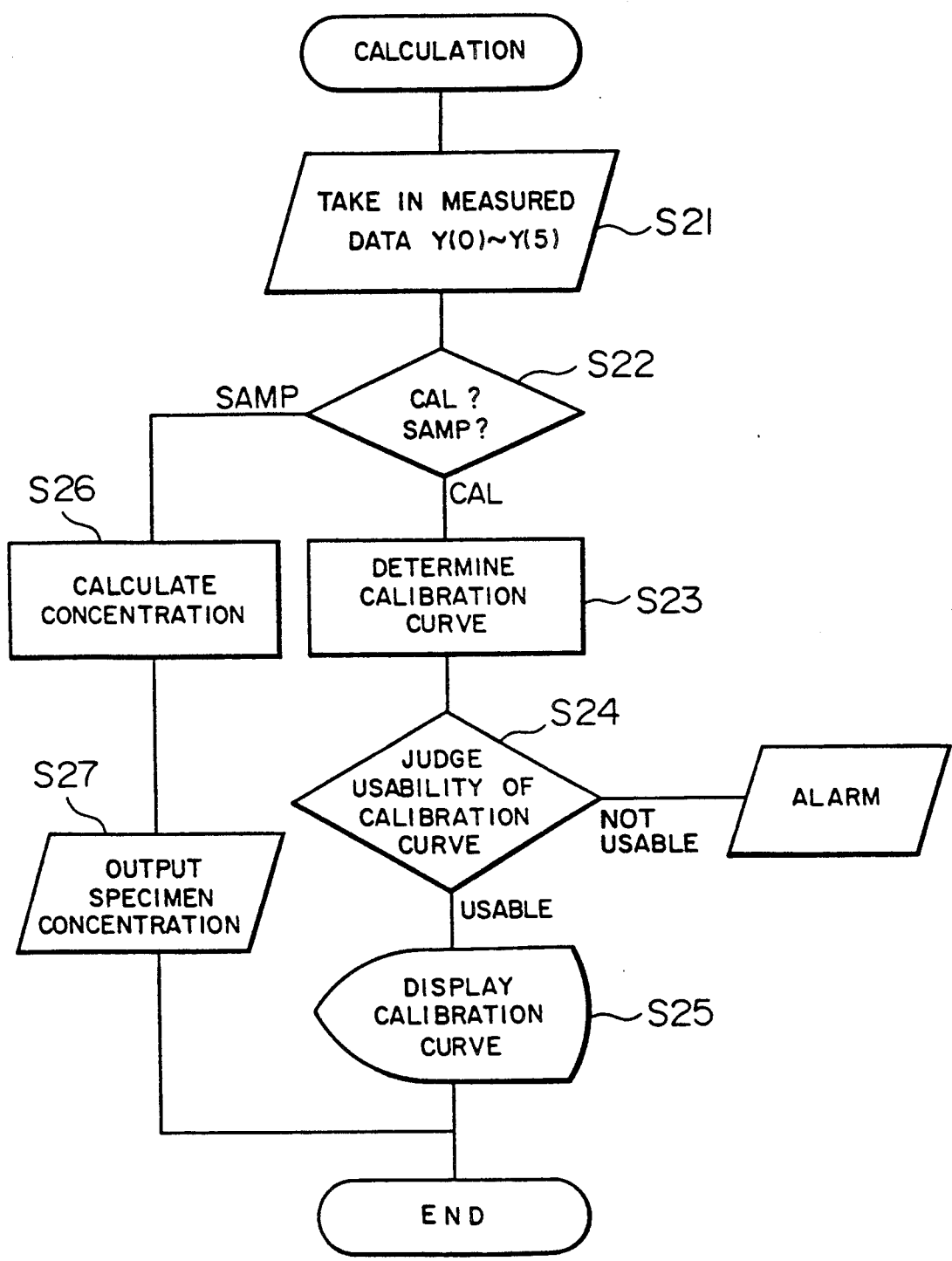
FIG. 2 is a flow chart illustrating a method of determining a calibration curve based on measured data (judging the usability of the calibration curve) and calculating the concentration of a specimen.

FIG. 2 is a flow chart illustrating a method of determining a calibration curve based on measured data (judging the usability of the calibration curve) and calculating the concentration of a specimen, the flow chart being used for explaining the embodiment of the calibration curve determining method of this invention. At step S21, measured data $Y(0)$ to $Y(11)$ are picked up. At step S22, it is checked if an object is a standard substance or a specimen. In case of a standard substance, a calibration curve is determined at step S23. At step S24, the determined calibration curve is checked if it is usable or not. If usable, the calibration curve is displayed at step S25. In case of a specimen at step S22, the concentration is calculated at step S26, and the specimen concentration is outputted at step S27.

A calibration curve for a standard substance determined in accordance with the flow chart shown in FIG. 1 is used for calculating the components of an actual living organism in accordance with the flow chart shown in FIG. 2. The calculated data may sometimes deviate greatly from the calibration curve obtained by the method shown in the flow chart of FIG. 1 (one of the reasons for this may be attributable to a degraded reagent). In such a case, the calibration curve is judged as not usable at corresponding flow step S24 without using such calibration curve, and a new calibration curve is again determined.

Figure 3:
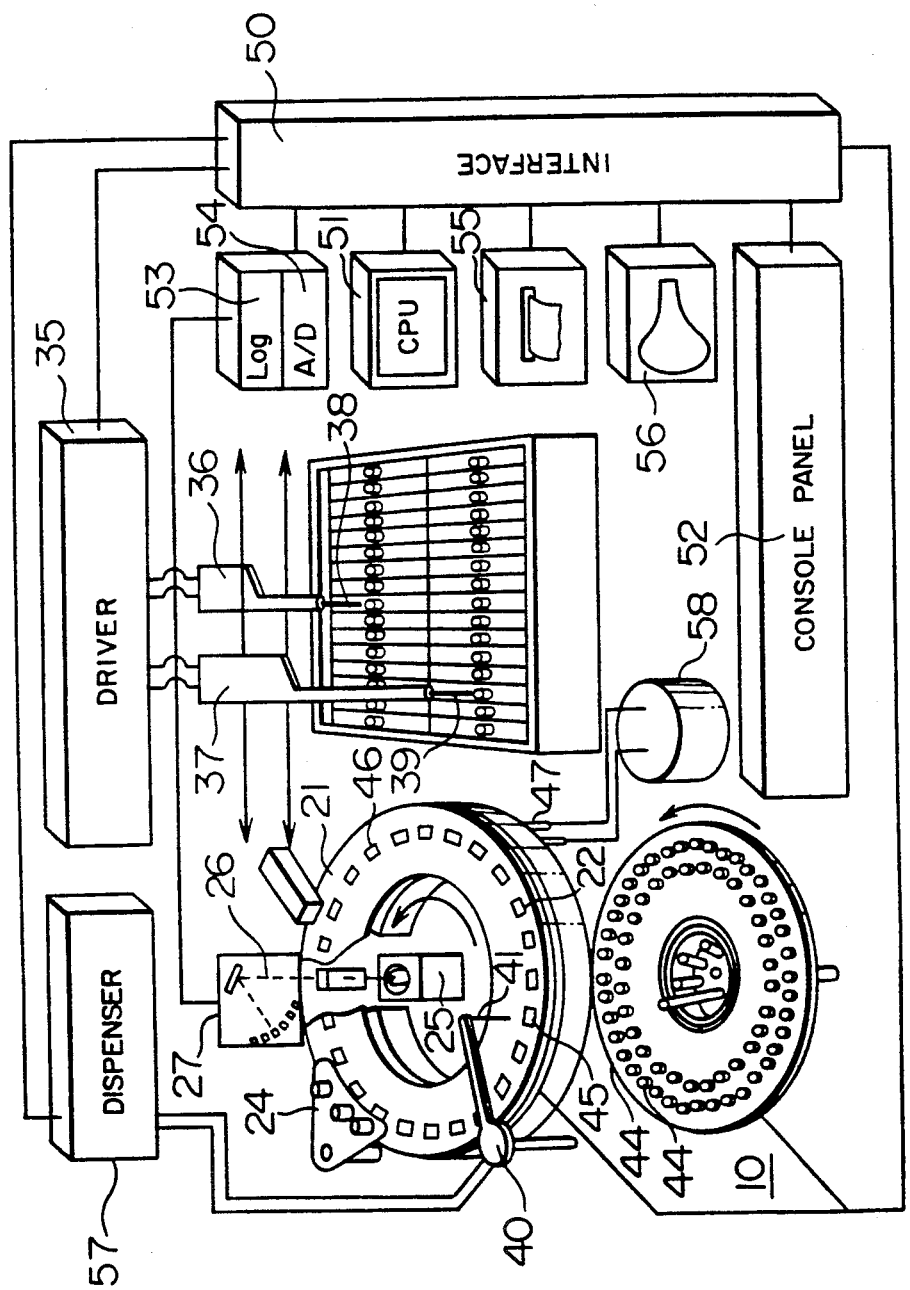
FIG. 3 is a schematic view showing the structure of an embodiment of an automatic analyzer for automatically analyzing the components of living a organism by using a calibration curve obtained by the calibration curve determining method of this invention.

Next, the automatic analyzer using the calibration curve determining method of this invention will be described. FIG. 3 shows the structure of an embodiment of the automatic analyzer according to this invention. Referring to FIG. 3, there is provided a sampling disk 10 on which a plurality of standard substances having different concentrations for respective test items can be mounted, with a plurality of standard substances for each test item being consecutively disposed one after another. A reaction disk 21, mounted rotatably, has at its outer circumferential portion a plurality of reaction vessels 22 serving also as measuring cells. A standard substance (sample) is carried out from a sample container 44 to a sampling probe 41 of a pipette 40. A reagent is dispensed with probes 38, 39 mounted at the end of dispensers 36, 37, the dispensers being movable in the direction indicated by a bi-directional arrow. A spectroscope 27 is constructed of a plurality of detectors for measuring a plurality of wavelengths at a same time. The spectroscope 27 is mounted facing a light source lamp 25 so that a train of reaction vessels 22 passes through a light beam 26 from the light source lamp 25 while the reaction disk 21 rotates counter clockwise. The light beam 26 is arranged to transmit thru the center of a reaction vessel, e.g., a 31st vessel 46 as counted clockwise from an ejection site 45 when the reaction disk 21 stops. A solution drain device and a cleaning device 24 are disposed between the light beam 26 site and ejection site 45.

The overall arrangement of a controller is constructed of a multiplexer, logarithmic conversion amplifier 53, A/D converter 54, read-only memory ROM, random access memory RAM, printer 55, console panel 52, and mechanical component driver 35. The A/D converter 54 is connected further to a central processing unit CPU 51 via an interface 50. CPU 51 made of a microcomputer controls the whole apparatus including its mechanical system, and performs all data processing including such as determining a calibration curve through the above-described multi-regression, concentration calculation and the like.

Figure 4:
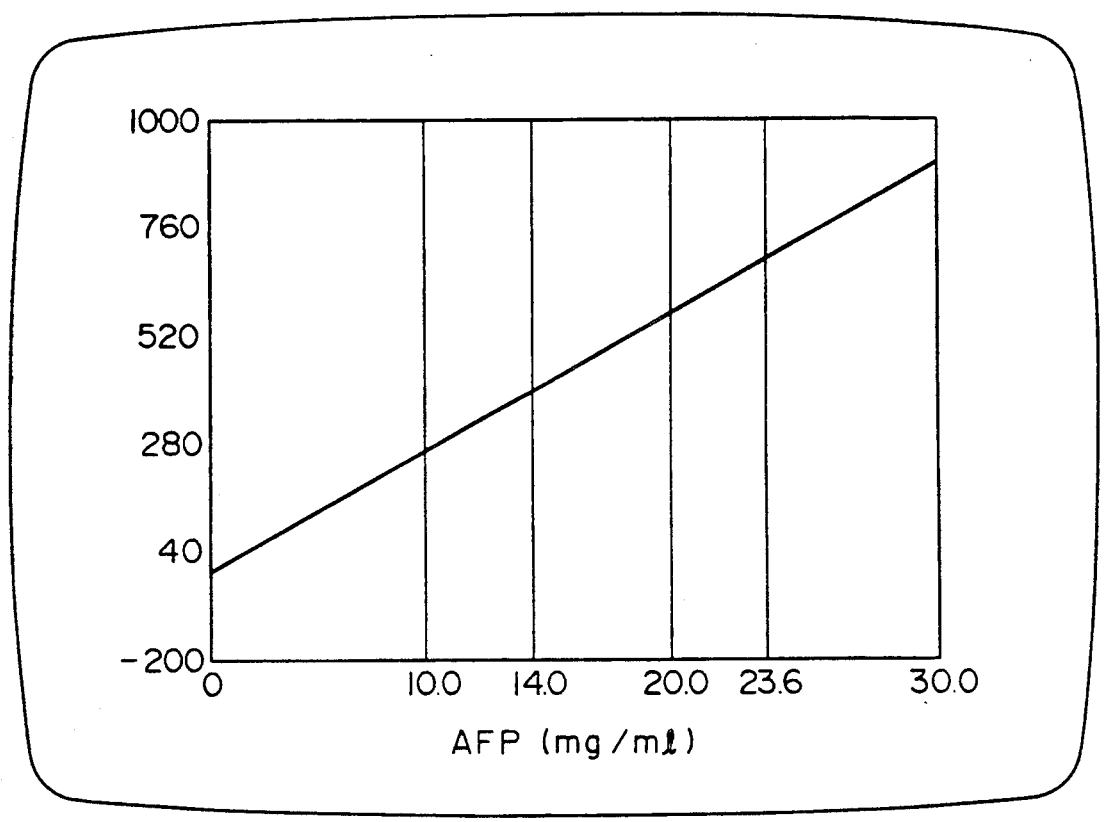
FIG. 4 shows an example of a calibration curve displayed on a display device.

Reference numeral 56 represents a display device on which displayed is a calibration curve such as shown in FIG. 4 for measuring a cancer marker $\alpha$-fetoprotein. Reference numeral 57 represents a dispenser for a reagent, and 58 a constant temperature oven.

Next, the operation of the embodiment shown in FIG. 3 will be described.

As a sample vessel 44 containing an object standard substance (sample) such as a cancer marker, substances associated with infectious disease and the like, is moved to the sampling site, the tip of the probe 41 of the pipette 40 is immersed into the sample vessel 44 to suck a predetermined amount of blood serum and hold it within the probe 41. Thereafter, the probe 41 is moved to the ejection site 45 of the reaction disk 21 to eject out the blood serum held in the probe 41 into the reaction vessel 22 at the ejection site 45. After the above sampling operation, the reaction disk 21 starts counter clockwise spontaneous rotation and continues it until the reaction vessels 22 larger in number by one than all of the reaction vessels 22 pass the ejection site.

With the counter clockwise rotation of the reaction disk 21, the reaction vessel 22 containing the sample which was sampled by the above sampling operation now stops at a position one pitch of the reaction vessels in advance from the ejection site 45 in the counter clockwise direction. During rotation of the reaction disk 21, all the reaction vessels 22 on the disk 21 pass through the light beam 26. The spectroscope 27 thus measures absorptivity and outputs data signals to a multiplexer whereat a data signal having an object wavelength is selected and supplied via the A/D converter to CPU 51 and stored in RAM.

Assuming that the time while the reaction disk 21 rotates and stops is 20 seconds, for example, then the above operation is repeated cyclically for 20 seconds at each cycle. As the cycles increase, the position of the reaction vessel 21 containing the sample advances one pitch after another in the counter clockwise direction when the disk 21 stops. A reagent is ejected out by the dispenser 36, 37 into the reaction vessel 22 containing the sample when it is stopped at the ejection site 46, 47 after having been rotated counter clockwise one pitch after another on the reaction disk 21. Thus, for a particular object sample, a first stage reaction starts upon application of a first reagent at the ejection site 47, and a second stage reaction starts upon application of a second reagent at the ejection site 46. Assuming that the stop time and rotation time of the reaction disk 21 during one cycle are 4.5 seconds and 15.5 seconds, respectively, the reaction processes of the object sample is measured 31 times every 20 seconds, and the measured data for 10 minutes are stored in RAM. CPU 51 operates under control of the programs (refer to FIGS. 1 and 2) stored in ROM to sample 31 measured data from RAM and process the data.

Five or six standard substances, for example, required for each test item in determining a calibration curve are consecutively disposed on the sample disk 10 so that the plurality of standard substances having different concentrations for the test item are carried out to the reaction vessel 22 plural times (e.g., plural times corresponding to weighting) automatically and consecutively. In determining a calibration curve for a substance having no linear relation to the concentrations, it is essential to sample and measure standard substances having different concentrations plural times, which the present apparatus can realize. The reaction processes of the plurality of standard substances are measured for 10 minutes as described above, and the measured data are stored for respective test items to be used for determining a calibration curve having a linear relation to concentrations.

According to the present invention described above, it is possible to determine a calibration curve having a weighted portion within a particular concentration range. Therefore, the cutoff value to be used in the analysis of the components of living organisms can be measured with high precision.

We claim:
1. An automatic analyzer, comprising:
   a sample feeding unit having means for containing reaction solutions of a plurality of standard substances having different concentrations;
   sampling and analyzing means for sampling and analyzing the reaction solutions of the standard substances plural times, including means for outputting data corresponding to the different concentrations;
   central processing means for receiving said data output from said sampling and analyzing means, including:
   first means for partially weighting said data by processing a part of said data that corresponds to a predetermined range of said different concentrations to obtain additional data in a predetermined amount that exceeds an amount of said data output by said sampling and analyzing means for said predetermined range;
   second means for storing said data together with said additional partially weighted data in memory;
   third means for processing the data stored by said second means;
   fourth means for calculating a calibration curve from the data processed by said third means;
   fifth means for outputting said calibration curve data calculated by said fourth means;
   means for receiving said calibration curve data and for displaying the calibration curve; and
   said sampling and analyzing means further for sampling and analyzing reaction solutions of said plurality of standard substances in unknown concentration to identify the unknown concentration based on said calibration curve.

2. A method of analyzing including determining a calibration curve for an analyzer, comprising the steps of:
   sampling reaction solutions for a plurality of standard substances having different concentrations;
   analyzing the reaction solutions sampled in said sampling step to obtain sets of data, each said set corresponding to a respective one of the different concentrations;
   partially weighting the analysis data by multiplying at least a single said set of the analysis data corresponding to a specific one of the different concentrations of reaction solutions by a predetermined multiplier to obtain a plurality of data corresponding to said specific one of the concentrations of reaction solutions;
   storing said sets of data and said plurality of data corresponding to said specific one of the concentrations of reaction solutions together;
   processing said stored data by means of a least-squares method and thereafter generating a calibration curve from said processed data; and
   sampling and analyzing the reaction solutions of said standard substances having an unknown concentration and determining the unknown concentration based upon said calibration curve.

3. A method according to claim 2, wherein said specific one of the concentrations of reaction solutions is a concentration near a limit value used as a criterion in a qualitative measurement with said analyzer.

4. A method of analyzing including determining a calibration curve for an analyzer, comprising the steps of:
   sampling reaction solutions for a plurality of standard substances having different concentrations;
   analyzing the reaction solutions sampled in said sampling step a predetermined number of times to obtain data corresponding to the different concentrations;
   partially weighting the analysis data by analyzing a specific one of the concentrations of reaction solutions a number of times greater than said predetermined number to obtain a plurality of analysis data for said specific one of the concentrations of reaction solutions;
   storing said analysis data together with said plurality of analysis data for said specific one of the concentrations of reaction solutions;
   processing said stored data by means of a least-squares method, and thereafter generating a calibration curve from said processed data; and
   sampling and analyzing reaction solutions of said standard substances having an unknown concentration and determining the unknown concentration based upon said calibration curve.

* * * * *